(12) United States Patent
Kanemaru et al.

(10) Patent No.: US 7,378,088 B2
(45) Date of Patent: May 27, 2008

(54) BASE MATERIAL FOR REGENERATING AN AIR SINUS AND REGENERATION METHOD THEREOF

(75) Inventors: Shin-ichi Kanemaru, Haitsu Hiruton 302, 20-7, Shimizudani-cho, Tennoji-ku, Osaka-shi 543-0011 (JP); Tatsuo Nakamura, Kyoto (JP); Hisayoshi Kojima, 13-26, Oomiya, Yakushiyamahigashi-cho, Kita-ku, Kyoto-shi 603-8474 (JP); Yasuhiko Shimizu, Uji (JP)

(73) Assignees: Shin-ichi Kanemaru, Osaka (JP); Hisayoshi Kojima, Kyoto (JP)

( * ) Notice: Subject to any disclaimer, the term of this patent is extended or adjusted under 35 U.S.C. 154(b) by 365 days.

(21) Appl. No.: 10/841,691

(22) Filed: May 6, 2004

(65) Prior Publication Data

US 2005/0002911 A1 Jan. 6, 2005

Related U.S. Application Data

(63) Continuation-in-part of application No. PCT/JP01/09673, filed on Nov. 6, 2001, now abandoned.

(51) Int. Cl.
*A01N 63/00* (2006.01)
*C12N 11/00* (2006.01)

(52) U.S. Cl. .............. 424/93.7; 424/423; 435/174; 435/180; 435/182

(58) Field of Classification Search .......... 424/93.7, 424/423; 435/174, 180, 182
See application file for complete search history.

(56) References Cited

U.S. PATENT DOCUMENTS

| 5,863,531 | A | 1/1999 | Naughton et al. ......... 424/93.7 |
| 6,454,811 | B1 * | 9/2002 | Sherwood et al. ....... 623/23.76 |
| 7,011,829 | B2 * | 3/2006 | Kanemaru et al. ........ 424/93.7 |
| 7,163,965 | B2 * | 1/2007 | Sotome et al. ............... 521/64 |
| 7,226,904 | B2 * | 6/2007 | Schneider et al. ............. 514/8 |

FOREIGN PATENT DOCUMENTS

JP 10-234844 9/1998

OTHER PUBLICATIONS

Jin et al., Effects of geometry of hydroxyapatite as a cell substratum in BMP-induced ectopic bone formation, Sep. 5, 2000, J. Biomed Mater Res, vol. 51, No. 3, pp. 491-499.*
Feb. 5, 2002 International Search Report for International Application No. PCT/JP01/09673.
P.D. Costantino, C.D. Friedman et al., "*Hydroxyapatite Cement. I. Basic Chemistry and Histologic Properties*" Arch. Otolarngol Head Neck Surg., vol. 117, No. 4, p. 379 (1991) (Abstract Only).
Kraut et al., "Composite bone graft augmentation for maxillary implant reconstruction: Clinical Report" Implant Dentistry vol. 2(4) 257-262 (1993).
Grote, "Results of Cavity Reconstruction With Hydroxyapatite Implants After 15 Years," The American Journal of Otology vol. 19:565-568 (1998).
Quinones et al., "Maxillary sinus augmentation using different grafting materials and osseointegrated dental implants in monkeys. Part II. Evaluation of porous hydroxyapatite as a grafting material," Clinical Oral Implants Res. vol. 8(6):487-496 (1997).
Kuboki et al., "Geometry of Artificial Extracellular Matrices: a New Paradigm from Dental Tissue Engineering," Dentistry in Japan vol. 37:42-50 (2001).
Jin et al., "Geometric factors in the hydroxyapatite cell-substratum controlling BMP-induced ectopic bone formation," Hokkaido J. Dent. Sci. 21:32-42 (2000).

* cited by examiner

*Primary Examiner*—Jon Weber
*Assistant Examiner*—Abdel A Mohamed
(74) *Attorney, Agent, or Firm*—Edwards Angell Palmer & Dodge LLP; David G. Conlin; Jonathan M. Sparks

(57) ABSTRACT

The instant invention provides a base material characterized by having a continuous three-dimensional honeycomb structure for regenerating an air sinus. The invention further provides methods for regenerating an air sinus using the base material. The base material has a composition and a structure that is similar to the wall and bone structure which allows it to becomes a scaffold of the regeneration of the mucosa tissue covering the surface of an air sinus.

8 Claims, No Drawings

BASE MATERIAL FOR REGENERATING AN AIR SINUS AND REGENERATION METHOD THEREOF

This application is a continuation-in-part of PCT/JP01/09673, filed on Nov. 6, 2001, now abandoned.

TECHNICAL FIELD

The present invention relates to a base material for regenerating an air sinus having a physiological function of a human body and a regeneration method thereof.

BACKGROUND ART

There are many air sinuses in a human body. Particularly, paranasal sinuses such as genyantrum and cavity of middle ear and so forth are present symmetrically in the face and the head, which are elements influencing on countenance and the shape of head.

The structural characteristics of these air sinuses are that the circumstance of every air sinus is surrounded by (a) bone(s) and the surface is covered by a thin mucosa, and these characteristics are connected with important physiological functions of the air sinus.

Although there are some different points in functions between a paranasal sinus and a cavity of middle ear, major physiological functions that an air sinus have are gas exchange ability and secretion of a substance, excretion of a metabolic decomposition product and so forth. When these functions are disordered, a disease such as paranasal sinus or tympanitis would be caught.

The treatments for these diseases can be divided into the conservative treatment (drug therapy) and the surgical treatment, and the former is intended to recover by a drug a mucosa in an air sinus which has been injured morbidly and has lapsed into a degeneration, and the latter is selected and applied for a disease which does not respond to the former and which is refractory. However, if you contract sinusitis or tympanitis over and over from the infant period, an air sinus by nature would not sufficiently be developed and a small air sinus which insufficiently has only necessary physiological functions would be formed, which results in being unable to recover from the disease completely.

Further, even if the removal of a seat of a disease in an air sinus is performed surgically, if the physiological functions are not recovered, it leads to a recurrence of the disease or to make a cause to induce another disease. That is why some people think that even an operation has no cure for sinusitis or tympanitis. That is, there is no idea or conception of regeneration of an air sinus having physiological functions in the conventional art.

Therefore, it is worth providing a means to recover completely from these diseases by newly forming the air sinus and by regenerating simultaneously also the physiological functions.

DISCLOSURE OF THE INVENTION

This invention is intended to the regeneration of an air sinus having a function which is not only morphologically important but also physiologically important, to provide a base material for regenerating a wall of an air sinus having a composition and a structure similar to the wall and bone structure which becomes a scaffold of the regeneration of the mucosa tissue covering the surface of an air sinus, and to provide method for regenerating an air sinus using said base material for regeneration.

That is, the present invention relates to:
1. a base material for regenerating an air sinus characterized by having a continuous three-dimensional honeycomb structure and having bioavailability;
2. a base material for regenerating an air sinus according to above mentioned 1 wherein the porosity is 1 to 99%;
3. a base material for regenerating an air sinus according to above 1 or 2, wherein the surface is covered with a collagen;
4. a base material for regenerating an air sinus according to any one of above 1 to 3, which is filled with mucosa cells of an air sinus;
5. a base material for regenerating an air sinus according to above 4, which is further filled with stromal cells;
6. method for regenerating an air sinus characterized by inserting and anchoring a base material for regenerating an air sinus according any one of above 1 to 5 into a subject tissue and immobilizing the base material ; and
7. method according to above 6, wherein the air sinus to be regenerated is an air sinus in a human body such as nose, paranasal sinus, cavity of middle ear or mastoid air cell.

BEST MODE FOR CARRYING OUT THE INVENTION

The base material for regeneration of the invention is characterized by having a continuous three-dimensional honeycomb structure, and having bioavailability. Here, three-dimensional honeycomb structure means a structure where each honeycomb does not form an independent cavity (an occluded cavity) but has communication with the outside.

The base material for regenerating an air sinus of the invention is not especially restricted as long as it has a three-dimensional honeycomb structure and it is a material having bioavailability, and it is preferably a material having a certain degree of strength.

As such a material, an autologous bone or a porous ceramics can be raised, and the porous ceramics includes calcium phosphate series ceramics (such as hydroxyl apatite, tricalcium phosphate and so forth), alumina ceramics, bioglass and so forth. The autologous bone, hydroxyl apatite and alumina are preferable as a material.

The overall structure of the base material for regeneration of the invention forms basically a three-dimensional honeycomb structure, but the density of the honeycomb structure may vary to a certain degree depending on the conformation of the air sinus to be regenerated. That is, for regeneration of paranasal sinus and so forth, it is desirable to use a base material for regeneration having possible loosest structure, in another, in the case of regeneration of mastoid air cell, it is desirable to use a base material for regeneration having a more tight structure rather than the case of paranasal sinus.

The porosity ratio of the base material for regeneration of the invention is 1 to 99%, preferably 3 to 95%, more preferably 60 to 90%. The porosity ratio of the base material for regeneration can be measured by Scanning Electron Microscope observation.

The base material for regeneration of the invention may take various conformations, for example, it can be a conformation of plate type, cube, rectangular parallelepiped, circular cylinder, block or film.

The surface of the base material for regeneration of the invention is preferably covered by collagen for the purpose of providing a scaffold where mucosa cells of an air sinus is easy to cover the surface of the base material for regeneration. The various types of collagen mentioned later can be used as the covering collagen. The covering by collagen can be performed normally, for example, by dipping into a hydrochloric acid solution of collagen. The covering amount of the collagen is 0.1 to 10% by weight, preferably 1 to 3% by weight corresponding to the base material for regeneration.

The base material for regeneration of the invention is preferably filled with mucosa cells of the air sinus to be regenerated. The mucosa cell to be filled can be obtained by collecting a mucous membrane from middle ear, nose, oral cavity and so forth, of a human who is required the regeneration of the air sinus, and carrying out a cell culture. The base material for regeneration is filled with the obtained mucosa cells. The number of the mucosa cells to be filled is several hundreds to hundreds of millions, preferably several hundreds thousands to several millions per 1 gram of the base material for regeneration.

The base material for regeneration of the invention is preferably filled with BSCs (bone marrow derived stromal cells) in addition to the mucosa cells of the air sinus. The mucosa cells and BSCs can be obtained, for example, by carrying out a three-dimensional mixed culture in collagen of cultured mucosa cells and stromal cells which is collected from selectively cultured bone marrow. The base material for regeneration is filled with the mucosa cell and the stromal cell obtained in this manner. The number of the mucosa cell to be filled is the same as mentioned above, and the number of stromal cell to be filled is several hundreds to hundreds of millions, preferably several hundreds thousands to several millions per 1 gram of the base material for regeneration.

In the present invention, as the collagen to be used for covering the base material for regeneration and for culturing cells, various types of conventionally used collagen such as neutral solubilized collagen, acid solubilized collagen, alkali solubilized collagen or enzymatic solubilized collagen can be used, and enzymatic solubilized collagen which is treated with an enzyme such as pepsin, trypsin, chymotrypsin, papain or pronase is preferred. Because the telopeptide which is an antigen group in a collagen molecule would be certainly removed and the antigenicity would be almost removed.

The origin of these collagen is not especially specified and type I collagen obtained by extracting and purifying from a skin, a bone, a cartilage, a tendon or an internal organ of an animal such as a human, a cow, a pig, a rabbit, a sheep, a kangaroo, a bird or a fish, or a mixture of type I collagen and type III collagen can be used.

As the stromal cell to be used in the invention, a material from which hematopoietic cells have been removed by subculturing collected bone marrow can be used.

Concretely, a bone marrow collected by using a puncture needle from a sternum, an iliac bone, a long bone and so forth of a donor of the bone marrow (the patient himself/herself is preferred from the aspect of immunity) is cultured and proliferated by normal cell culture, for example, in an Eagle's Minimum Essential Medium (Eagle's MEM) which is added 10% FBS (fetal bovine serum). When a culture bottle is used, hematopoietic cells are removed in the process of exchanging the culture solution, and stromal cells come to increase on the bottom of the bottle in about a week.

Under a microscope, observing said culture bottle and when the cells have been proliferated sufficiently at the bottom of said culture bottle, the cells are torn off by using an enzyme (trypsin). The obtained cell suspension is subjected to an usual cell counter such as Metallized Counting Chamber (manufactured by Becton Dickinson Co. Ltd.) to confirm the number of cells. Further, $10^5$-$10^7$ cells can be collected from a middle size culture bottle (260 ml).

In the present invention, filling of the stromal cell can be carried out by mixing the stromal cell (suspension) prepared as described above with hydrochloric acid solution of collagen so as to be a predetermined cell density (for example, $10^5$-$10^7$ cells/ml collagen), which is filled into the base material for regeneration.

Method for regenerating an air sinus of the invention is characterized in that any one of above mentioned base material for regenerating an air sinus is inserted into the tissue to be regenerated and is immobilized.

The amount of the base material for regeneration to be inserted into the subject tissue and be immobilized may vary depend on the size of the air sinus to be regenerated, for example, the amount is several grams to several hundred grams, preferably several grams to several dozen grams.

The insertion of the base material for regeneration into a subject tissue can be carried out, for example, by an operation under general anesthesia or under local anesthesia, and the immobilization of the base material for regeneration to the subject tissue can be carried out, for example, by immobilization by a suture thread or by immobilization by a surgical adhesive.

The air sinus to which the regeneration method of the invention can be applied involves, for example, nose, paranasal sinus (maxillary sinus, ethmoidal sinus, sphenoidal sinus), cavity of middle ear and mastoid air cell.

EXAMPLES

The invention is explained by examples as follows, however, the invention is not limited to them.

Example 1

1) Preparation of the Base Material for Regeneration

Two kinds of calcium phosphate series ceramics (hydroxyl apatite) having a blockish outward form of 3×3×2 cm with small continuous holes having a diameter of several hundred μm to 3 mm and having different porosities (50% and 80%) were used as the base material for regeneration. The hydroxyl apatite is covered with collagen using hydrochloric acid solution of collagen (pH=3, collagen concentration=1.0% by weight, Nippon Ham Co. Ltd.) obtained by enzymatically solubilizing a pig skin.

2) Filling Mucosa Cell and Stromal Cell into the Base Material and Culturing the Mucosa Cell (Culture of Mucosa Cells)

A mucosa from dog oral cavity was cut into a size of 1×1 cm, the mucosa was cut finely by a surgical knife on a petri dish with culture fluid, and mucosa cells were dispersed. A culture fluid that 10% fetal bovine serum is added to MEM culture media was used. A week later, mucosa cells were proliferated on the bottom of the petri dish. This was torn off by trypsin, then this was washed with culture fluid to remove trypsin and centrifuged to concentrate the cell and then this was made to be a cell suspension using hydrochloric acid solution of collagen(pH=3, collagen concentration=1.0% by weight, Nipponham Co. Ltd).

(Culture of Stromal Cells)

Bone marrow fluid 1 ml was collected from a dog bone (femur or humerus) by a bone marrow puncture needle and was cultured in a bottle with culture fluid. Culture fluid that 10% fetal bovine serum is added to MEM culture media was used. The culture fluid was changed once in a three to five days and suspending hematocytes were removed. Adherent cells (stromal cells) spreaded over the bottom of the bottle 2-3 weeks later. This was torn off by trypsin and manipulated as performed in the culture of mucosa cells to make a cell suspension.

(Filling of Cell into Base Material)

Mucosa cell suspension (a million cells to ten million cells/ml) was sucked into an injection syringe, the mucosa cell suspension was dropped onto the base material for regeneration with a thick needle for syringe of about 18 G and the suspension was made sink into all over the base material.

A mixture of mucosa cell suspension and stromal cell suspension in an equal amount each other was sank into another regeneration base material all over in a same manner as mentioned above.

The two kinds of regeneration base materials were cultured for three weeks on petri dishes in culture fluid of an amount where whole of the base material was soaked. Three weeks later, it was picked up and fixed with formalin, and the pathological segment was observed.

3) Results

The mucosa cell collected from the mucosa membrane in the oral cavity of a dog was cultured as mentioned above and how the base material for regeneration was covered by the mucosa membrane was observed and investigated. The mucosa membrane coverage ratio was not greatly influenced in the range of the porosity ratio of the base material for regeneration used this time. Concerning the base material for regeneration where the stromal cells and the mucosa cells were simultaneously filled and the regeneration material where only the mucosa cells were filled, both of them were covered by the mucosa cell, but it was confirmed by the microscopic observation of the pathological tissue that the number of the surface cell was clearly larger in the former one and a better coverage ratio was obtained.

Example 2

1) Preparation of the Base Material for Regeneration

The base material for regeneration was prepared by filling cultured cell (one where the stromal cell and the mucosa cell were used simultaneously and another where only the mucosa cell was used) in the same manner as mentioned in Example 1-1) and 1-2).

2) Insertion of the Base Material for Regeneration and Immobilization Thereof, and Observation of Covering Degree with Mucosa Under general anesthesia, the metope of a dog was cut open horizontally and the frontal sinus was exposed by making holes in the size of around 1×2 cm at left and right side of upper part of eyebrows on the skull. The base material for regeneration prepared in above mentioned 1) was inserted into the left and right frontal sinuses of the same dog and the skin was stitched up. The size of the holes were made almost the same as the size of the base material for regeneration. The dog was sacrificed about 6 months later and the degree of mucosa coverage in the air sinus was observed. Further, radiographies were taken twice and the internal condition of the air sinus was observed, in the six months up to the sacrifice.

3) Results

Both of them were covered by mucosa cells, but a better coverage ratio of mucosa cell was obtained with the base material for regeneration which was filled with the stromal cell and the mucosa cell simultaneously than that with only the mucosa cell.

INDUSTRIAL APPLICABILITY

Although only a temporal bone or a paranasal sinus as a single sinus, particularly formation of mucosa on the surface of ethmouidal sinus is supposed to be insufficient as a gas exchange ability, if a network mucosa honeycomb which spreads over all space in a paranasal sinus or a temporal bone can be constructed by using an alternative bone having a contiguous three-dimensional honeycomb structure as the present invention, a structure where the surface area has been expanded and a sufficient gas exchange ability is obtained, and which is physiologically more natural and close to cavity of middle ear, can be obtained.

Therefore, with the present invention, it is possible that chronic sinusitis, chronic otitis media, cholesteatoma, adhesive otitis and so forth which so far have been considered as intractable would be healed, and these treatments would be revolutionized.

The invention claimed is:

1. A base material for regenerating an air sinus which comprises an autologous bone or a porous ceramics each having a continuous three-dimensional honeycomb structure capable of regenerating an air sinus and having bioavailability, and wherein the material has a porosity ratio of 60 to 95% and a surface of the material is covered with enzymatic solubilized collagen.

2. The base material according to claim 1, wherein the collagen is solubilized by treatment with an enzyme selected from the group consisting of pepsin, trypsin, chymotrypsin, papain and pronase.

3. A material for regenerating an air sinus comprising the base material according to claim 1, wherein the porous ceramics is at least one selected from the group consisting of calcium phosphate ceramics, alumina ceramics and bioglass the surfaces of which are covered by the enzymatic solubilized collagen in an amount of 0.1 to 10% by weight based on the amount of the base material, and mucosa cells are filled into the continuous three-dimensional honeycomb structure of the base material in a number of hundreds to hundreds of millions per 1 g of the base material.

4. The base material according to claim 3, wherein the porous ceramics is covered by the enzymatic solubilized collagen in an amount of 1 to 3% by weight.

5. The base material for regenerating an air sinus according to claim 1, wherein the base material is for filling with mucosa cells of an air sinus.

6. The base material for regenerating an air sinus according to claim 5, wherein the base material is for further filling with stromal cells.

7. A method for regenerating an air sinus which comprises the steps of: inserting a base material for regenerating an air sinus according to any one of claims 1, 5, and 6 into a subject tissue and immobilizing the base material.

8. The method for regenerating an air sinus according to claim 7, wherein the air sinus to be regenerated is an air sinus in a human body selected from the group consisting of nose, paranasal sinus, cavity of middle ear and mastoid air cell.

* * * * *